US00PP14725P2

(12) United States Plant Patent
Hofmann

(10) Patent No.: US PP14,725 P2
(45) Date of Patent: Apr. 20, 2004

(54) NEW GUINEA IMPATIENS PLANT NAMED 'FISUPNIC CORAL ICE'

(50) Latin Name: *Impatiens hawkeri*
Varietal Denomination: Fisupnic Coral Ice

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/452,974

(22) Filed: Jun. 3, 2003

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisupnic Coral Ice', characterized by its outwardly spreading and uniformly mounded plant habit; tall growth habit; freely branching and freely flowering habit; medium green-colored foliage; and large, rounded, light red-colored flowers with white-colored centers that are positioned just at, above or beyond the foliage.

1 Drawing Sheet

Botanical classification/cultivar designation: *Impatiens hawkeri* cultivar Fisupnic Coral Ice.

BACKGROUND OF THE INVENTION

The present Invention relates to a new and distinct cultivar of New Guinea Impatiens plant, botanically known as *Impatiens hawkeri*, and hereinafter referred to by the name 'Fisupnic Coral Ice'.

The new Impatiens is a product of a planned breeding program conducted by the Inventor in Hillscheid, Germany and Galder, Gran Canaria, Spain. The objective of the breeding program is to develop new vigorous Impatiens cultivars with medium flowering response and large rounded flowers with attractive coloration.

The new Impatiens originated from a cross-pollination made by the Inventor during the spring of 1999 of a proprietary seedling selection of *Impatiens hawkeri* identified as code number 98-4070-2, not patented, as the female, or seed, parent with the *Impatiens hawkeri* Fisnics Scarlet Blush, disclosed in U.S. Plant Pat. No. 13,227, as the male, or pollen, parent. The cultivar Fisupnic Coral Ice was discovered and selected by the Inventor as a flowering plant within the progeny of the stated cross-pollination in a controlled environment in Galder, Gran Canaria, Spain in April, 2000.

Asexual reproduction of the new cultivar by terminal cuttings taken in Galder, Gran Canaria, Spain, since July, 2000, has shown that the unique features of this new Impatiens are stable and reproduced true to type in successive generations.

SUMMARY OF THE INVENTION

The following traits have been repeatedly observed and are determined to be the unique characteristics of 'Fisupnic Coral Ice'. These characteristics in combination distinguish 'Fisupnic Coral Ice' as a new and distinct Impatiens cultivar:

1. Outwardly spreading and uniformly mounded plant habit; tall growth habit.
2. Freely branching and freely flowering habit.
3. Medium green-colored foliage.

4. Large, rounded, light red-colored flowers with white-colored centers that are positioned just at, above or beyond the foliage.

Plants of the new Impatiens can be compared to plants of the female parent selection. In side-by-side comparisons conducted by the Inventor in Hillscheid, Germany, plants of the new Impatiens differed from plants of the female parent selection in the following characteristics:

1. Plants of the new Impatiens were larger and more vigorous than plants of the female parent selection.
2. Plants of the new Impatiens had darker green-colored leaves than plants of the female parent selection.
3. Plants of the new Impatiens and the female parent selection differed in flower coloration as plants of the female parent selection had white-colored flowers.

Plants of the new Impatiens can be compared to plants of the male parent, the cultivar Fisnics Scarlet Blush. In side-by-side comparisons conducted by the Inventor in Hillscheid, Germany, plants of the new Impatiens differed from plants of the cultivar Fisnics Scarlet Blush in the following characteristics:

1. Plants of the new Impatiens were larger and more vigorous than plants of the cultivar Fisnics Scarlet Blush.
2. Leaves of plants of the new Impatiens were lighter green in color than leaves of plants of the cultivar Fisnics Scarlet Blush.
3. Plants of the new Impatiens and the cultivar Fisnics Scarlet Blush differed in flower coloration as plants of the cultivar Fisnics Scarlet Blush had red-colored flowers.

Plants of the new Impatiens can also be compared to plants of the cultivar Harmony Cherry Ice, not patented. In side-by-side comparisons conducted by the Inventor in Hillscheid, Germany, plants of the new Impatiens differed from plants of the cultivar Harmony Cherry Ice in the following characteristics:

1. Plants of the new Impatiens were taller than plants of the cultivar Harmony Cherry Ice.
2. Leaves of plants of the new Impatiens were longer than leaves of plants of the cultivar Harmony Cherry Ice.
3. Plants of the new Impatiens and the cultivar Harmony Cherry Ice differed in flower coloration as plants of the cultivar Harmony Cherry Ice had darker red-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisupnic Coral Ice' grown in a container.

DETAILED BOTANICAL DESCRIPTION

The cultivar Fisupnic Coral Ice has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers and the aforementioned photograph and following observations and measurements were taken about 11 weeks later. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisupnic Coral Ice.

Parentage:

*Female parent.*—Proprietary seedling selection of *Impatiens hawkeri* identified as code number K98-4070-2, not patented.

*Male parent.*—*Impatiens hawkeri* cultivar Fisnics Scarlet Blush, disclosed in U.S. Plant Pat. No. 13,227.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D in color.

Plant description:

*General appearance.*—Outwardly spreading and uniformly mounded plant growth habit; tall growth habit; freely branching habit; bushy appearance; freely flowering. Vigorous.

*Crop time.*—From a rooted cutting, about 9 to 10 weeks are required to produce finished flowering plants in 12-cm containers.

*Plant height.*—About 19.6 cm.

*Plant diameter or spread.*—About 45 to 50 cm.

*Lateral branches.*—Quantity per plant: About 9 to 11. Length: About 16 to 19 cm. Diameter: About 6 to 7 mm. Internode length: About 4.5 to 7.4 cm. Texture: Smooth, glabrous. Color: 144B overlain with 179A to 179B.

*Foliage description.*—Arrangement: Primarily in whorls. Length: About 12 to 15 cm. Width: About 3.3 to 3.5 cm. Shape: Elliptic. Apex: Acuminate. Base: Acute. Margin: Serrulate with ciliation. Texture: Smooth, slightly rugose; glabrous. Color: Developing foliage, upper surface: 137D. Developing foliage, lower surface: 138B. Fully expanded foliage, upper surface: 137B. Fully expanded foliage, lower surface: 138B. Venation, upper surface: 145A; towards the base, 181C. Venation, lower surface: 53C. Petiole: Length: About 2 to 4 cm. Diameter: About 3 to 4 mm. Texture: Smooth, glabrous. Color, upper surface: 181B to 181C. Color, lower surface: 53C.

Flower description:

*Flower type and flowering habit.*—Single, large, rounded, light red-colored flowers with white-colored centers. Freely and continuously flowering; usually about 6 to 9 flowers and flower buds per lateral branch. Flowers positioned just at, above or beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 to 10 weeks after planting.

*Flower buds.*—Length: About 2.5 cm. Diameter: About 1.8 cm. Shape: Ovoid. Color: 52A.

*Flower length.*—About 7.8 to 8 cm.

*Flower width.*—About 7.5 to 7.7 cm.

*Flower depth.*—About 5 to 10 mm.

*Petals.*—Quantity: Five per flower, imbricate. Length: Banner petals: About 3 cm. Lateral and base petals: About 3.7 to 4.2 cm. Width: Banner petal: About 4.3 cm. Lateral and base petals: About 3.1 to 3.3 cm. Shape: Cordate. Apex: Moderately lobed. Base: Attenuate. Margin: Entire. Aspect: Mostly flat. Texture: Smooth; satiny. Color: When opening, upper surface: 52A. When opening, lower surface: Between 52A to 52B. Fully opened, upper surface: 52B; towards the base, 155D. Fully opened, lower surface: 54B.

*Spur.*—Quantity: One per flower. Length: About 6.5 to 7 cm. Diameter: At apex: About 0.5 mm. At flower: About 2.5 mm. Aspect: Curved. Color: 53A to 53B.

*Peduncles.*—Length: About 6 to 6.5 cm. Diameter: About 2 mm. Texture: Smooth, glabrous. Strength: Strong, flexible. Color: 53B.

*Reproductive organs.*—Androecium: Stamen number: Five fused at anthers, hooded; filaments free. Anther length: About 6 mm. Anther shape: Obovate. Anther color: 46D. Pollen amount: Moderate. Pollen color: 8D. Gynoecium: Pistil quantity: One per flower. Pistil length: About 5 to 6 mm. Stigma color: 8D. Style color: 8D. Ovary: Five-celled. Ovary color: 143C.

*Seed/fruit.*—Seed and fruit development has not been observed.

Disease/pest resistance: Plants of the new Impatiens have not been observed to be resistant to pathogens and pests common to Impatiens.

Low temperature tolerance: Plants of the new Impatiens have been observed to tolerate night temperatures of 5° C. with 10° C. day temperatures.

It is claimed:

1. A new and distinct cultivar of New Guinea Impatiens plant named 'Fisupnic Coral Ice', as illustrated and described.

* * * * *

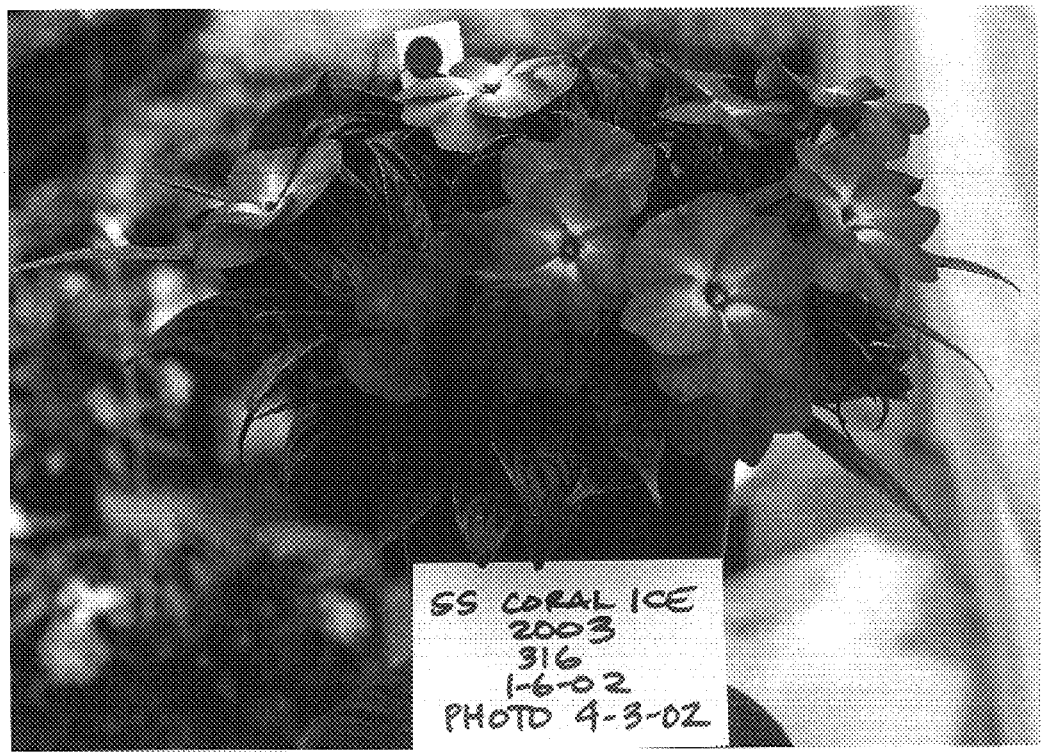
SS CORAL ICE
2003
316
1-6-02
PHOTO 4-3-02